United States Patent [19]
Israel et al.

[11] 3,956,099
[45] May 11, 1976

[54] CONTINUOUS PREPARATIVE ELECTROPHORESIS APPARATUS

[76] Inventors: Louis Israel, 2453 Farmers Ave., Bellmore, N.Y. 11710; Leslie Bernstein, 1 Aviemore Drive, New Rochelle, N.Y. 10804

[22] Filed: Dec. 23, 1974

[21] Appl. No.: 535,571

Related U.S. Application Data

[62] Division of Ser. No. 302,347, Oct. 30, 1972, Pat. No. 3,873,432.

[52] U.S. Cl. ..................... 204/299 R; 204/180 G; 204/180 S
[51] Int. Cl.[2] ................. G01N 27/00; G01N 27/26; G01N 27/40
[58] Field of Search ............ 204/180 G, 180 S, 299, 204/300

[56] References Cited
UNITED STATES PATENTS

| | | | |
|---|---|---|---|
| 2,992,979 | 7/1961 | Magnuson et al. | 204/300 X |
| 3,290,240 | 12/1966 | Neren | 204/299 |
| 3,305,471 | 2/1967 | Von Munchhausen et al. | 204/299 |
| 3,384,564 | 5/1968 | Ornstein et al. | 204/180 G |
| 3,594,294 | 7/1971 | Pretorius et al. | 204/180 G |
| 3,616,454 | 10/1971 | Levy | 204/299 |
| 3,699,033 | 10/1972 | Zeineh | 204/180 G |
| 3,755,121 | 8/1973 | Schultz | 204/180 G |
| 3,773,648 | 11/1973 | Van Welzen et al. | 204/299 |

*Primary Examiner*—Howard S. Williams
*Assistant Examiner*—A. C. Prescott
*Attorney, Agent, or Firm*—Darby and Darby

[57] ABSTRACT

Apparatus for continually separating mixtures of proteins or other charged particles of differing size, and/or weight, such as those present in a serum, using the principle of electrophoresis. A multi-celled separating unit has portions of the mixture to be separated applied by an applicator sequentially to the several cells of the unit. Separate collection compartments for the respective separated components are located with relation to the separating unit so that each compartment continually receives a single one of the components as it is separated out by the separating cells.

14 Claims, 16 Drawing Figures

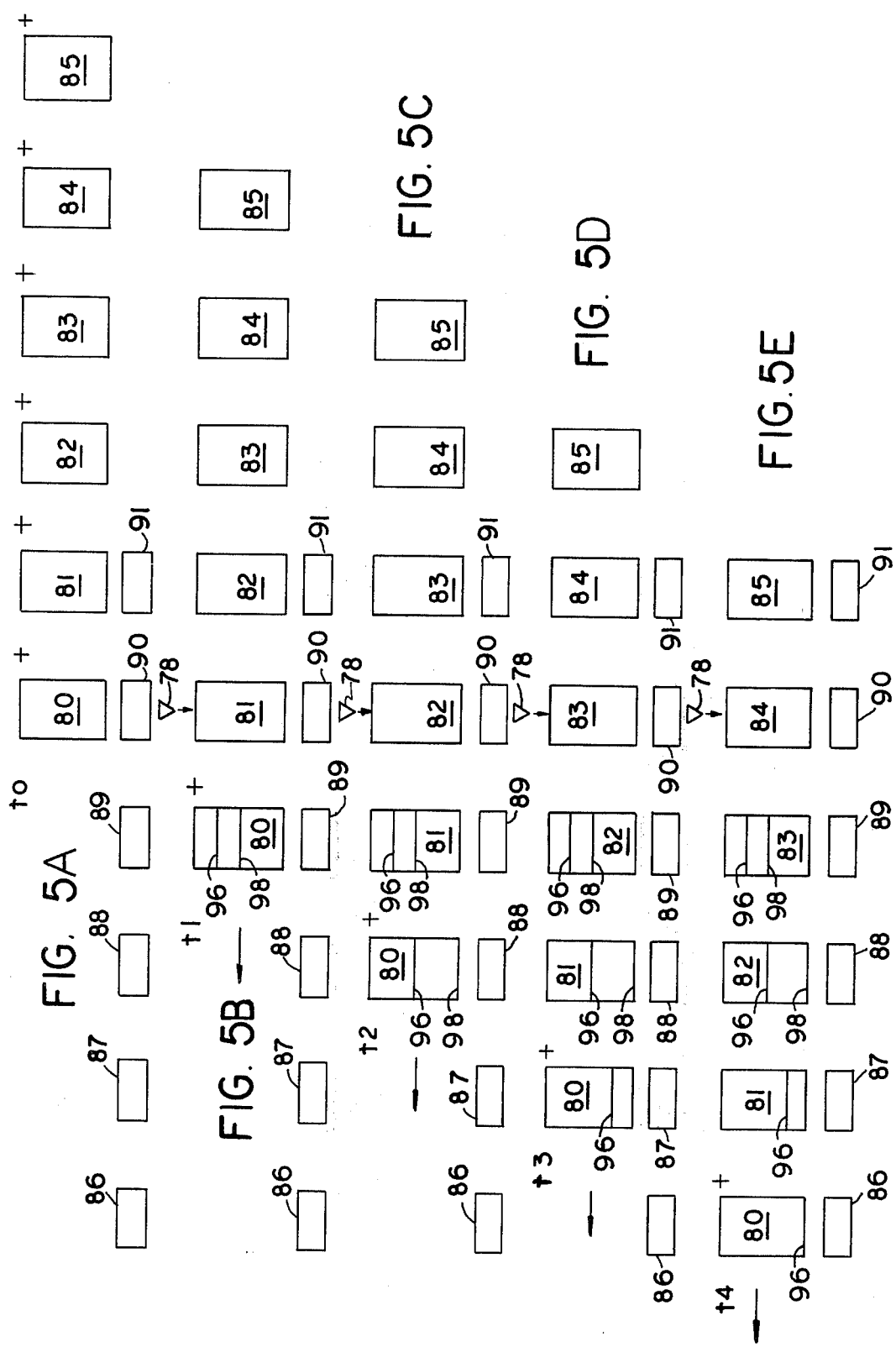

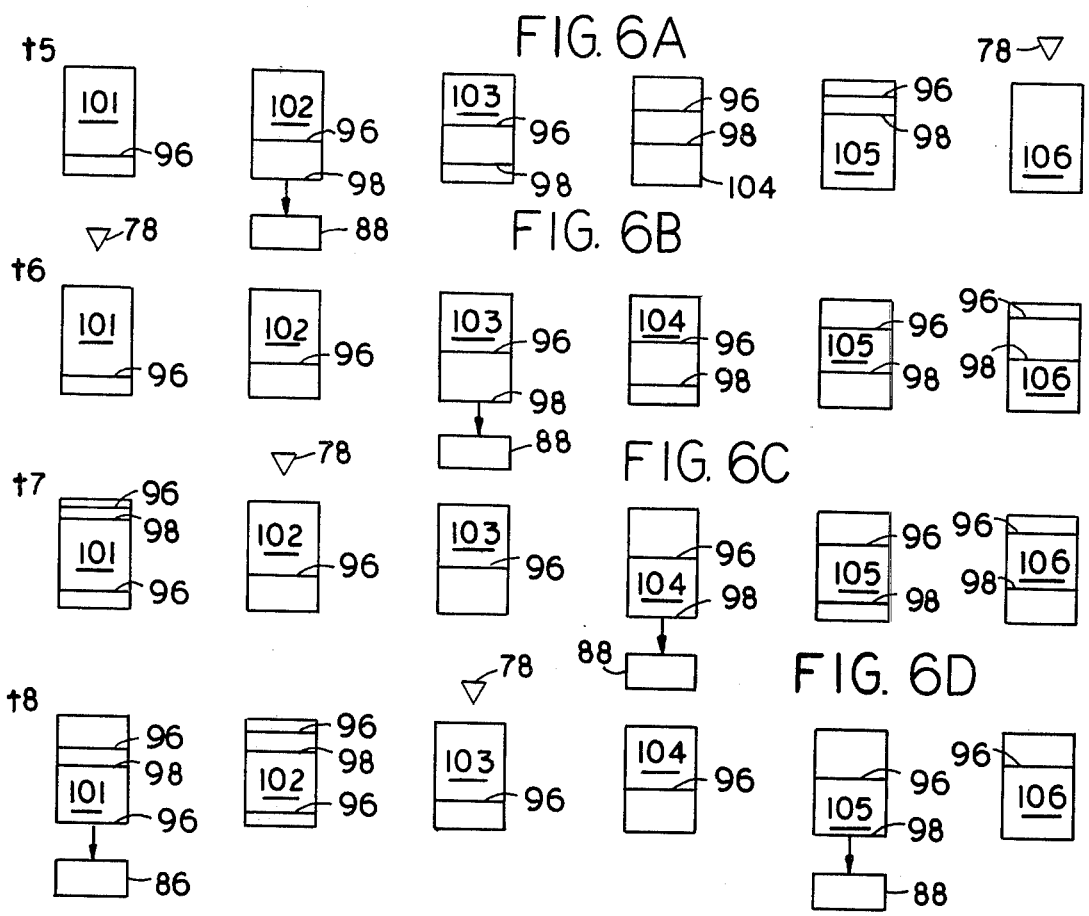
FIG. 6A
FIG. 6B
FIG. 6C
FIG. 6D
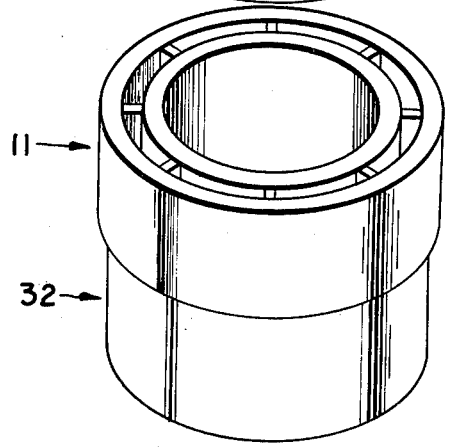
FIG. 7

CONTINUOUS PREPARATIVE ELECTROPHORESIS APPARATUS

This is a division of application Ser. No. 302,347, filed Oct. 30, 1972 now U.S. Pat. No. 3,873,432.

BACKGROUND OF THE INVENTION

Electrophoresis is a well known principle used in separating a mixture of components of differing molecular weight, and/or size, such as proteins, and has had particular applicability in the medical field in separating the components of blood serum for testing and in large-scale production of special protein products. The process also has wide applicability in the industrial separation and recovery of other mixed components.

In the electrophoresis process the mixture to be separated is applied to one end of a neutral supporting medium, such as paper, gel (acrylamide, starch or agar), or any of the other known supporting media. An electrical potential difference is induced between the end surfaces of the medium by a power source and transferred to the medium through an electrolyte or buffer solution. The different components in the mixture adopt electrical charges and have different constants of mobility in the medium in accordance with their charges, sizes or molecular weights and pH of the medium, and thus move at different rates in the medium under the influence of the electric field, thereby effectively becoming separated in space in the medium.

One of the major recognized disadvantages of the prior devices is their inability to continually automatically collect the different components of the mixture as they are separated by the supporting medium. The general method of operation is to apply a batch of the mixture to be separated to the supporting medium, wait for the components to separate, and then sequentially collect the components in different containers as they reach the bottom of the medium.

One attempt at increasing the speed of collecting the separated components (but still not automatically) uses a series of individual supporting media to simultaneously separate a series of applications of a mixture, or of different mixtures, as disclosed in U.S. Pat. No. 3,576,727 to B. L. Evott. While this increases the amount of mixture separated, it still maintains the same main disadvantage of the single-sample operation in requiring constant supervision for sequentially collecting the components at proper moments after they separate.

Other devices, such as the Brinkmann Preparative Electrophoresis System, which is commercially available, do provide apparatus for continuously separating the components of a mixture. Such a system, however, cannot use a supporting medium, as required in the most desirable systems, so as to obtain maximum accuracy and purity of separation. In the Brinkmann device, a buffer solution is fed in a continuous stream between a pair of closely spaced planar parallel plates, with an electrical field parallel to the plates and at right angles to the stream direction. As the mixture travels with the buffer flow, the components with different electrophoretic mobilities are driven by the electric field at different angles from the flow path and are collected at respective given points at the end of the planar plate opposite from that which the mixture was introduced. The apparatus is expensive, complicated, extremely bulky, requires sophisticated controls, and has limited separation capacity. Further, it requires bulk flow of electrolyte and components with high lateral rate of movement to be mixed at the lateral limiting membranes.

SUMMARY OF FUNCTIONAL OBJECTS

This invention is for an electrophoretic device which is capable of continually automatically separating and collecting the components of a protein or like mixture.

A separating unit is provided which includes an array of separating cells, the array preferably comprising a single supporting medium such as acrylamide gel supported between two walls forming a separating chamber. At equally spaced intervals along a top surface of the supporting medium, indentations or recesses are formed. The recesses prevent lateral flow of the mixture so as essentially to create individual inputs into the medium corresponding to the several cells. In an alternative embodiment, vertical inert partitions (such as made from plastic materials) may be used to delineate the several cells, either in conjuction with the recesses, or alone.

Surrounding the supporting walls of the cell array and in contact with the top surface of the supporting medium is an electrolytic buffer solution. The electrolyte is refrigerated to a temperature in the vicinity of 0°C – 25°C, so as to dissipate heat, prevent swelling of the gel, and destruction of the proteins. The electrolytic fluid at one end of the cell array is maintained at an electrical potential in the range of 200 to 500 volts with respect to the other end.

Adjacent the input ends of the cells of the supporting medium is located at least one applicator for applying the mixture to be separated sequentially to the separating cells. The applicator is capable of being operated so as to deposit either a constant flow for a given time interval or a batch of the input mixture to each of the separate cells in turn.

A collection unit is supplied adjacent the discharge ends of the cells, the unit comprising one or more collection compartments filled with an electrolytic buffer solution in contact with the bottom surface of the supporting medium and electrically insulated from the buffer solution in the separating unit. This buffer solution is maintained at an opposite electrical potential from that of the buffer solution in contact with the top surface of the separating medium, so as to create an electric field across the supporting medium. The collection compartments are arranged to collect the discharges from the several cells in sequence, each collection from any cell being made at a fixed time interval after the loading of the cell, so that one or more separated components is collected in that compartment.

In one form, each collection compartment comprises a connecting member adjacent the cell discharge ends with at least one aperture surrounded by a sealed membrane which permits the electrolytic buffer ions to enter the connecting member and come into contact with the lower surface of the supporting medium. The membrane bag, however, does not permit the separated components to escape from the collection compartment.

In operation in a preferred form, one of the separating cells in the separating unit is supplied with a fixed quantity of the mixture to be separated. After a fixed predetermined time interval a second batch of mixture is supplied to a second cell, and after like time intervals the successive cells are supplied with respective inputs.

The constants of mobility of the different components of the mixture will differ, and thus different components of the mixture will travel to the bottom of each separating cell, in essentially a vertical direction within the cell, in different times. For particular materials and under fixed conditions of electric field, the time that it takes each individual component to traverse each cell, however, is a constant.

It is therefore arranged that the collection of each cell discharge takes place a fixed time interval after the cell has been loaded, so that the collection under ideal conditions will be of only a single component, representing a preselected weight or size of protein molecule, for example. When the mobility rates of two component particles in a mixture are very similar it is possible that both particles will be deposited in a single collection compartment. If further separation of the two particles is desired, they may then be re-inserted into the separating unit setting different parameters, such as the pH of the electrolytic solution. (It is possible in a mixture of many components for 2 to enter one cell).

In a preferred arrangement, the operation is effected by having the loading point and the collection point fixed relative to one another, while the separating cell array is relatively movable with respect to the loading and collection points. If the separating cells are arranged in a generally circular configuration which rotates as a whole about a vertical axis, each component as it travels vertically within its particular cell will have a locus in space essentially in the shape of a helix. Since each like component takes the same amount of time to traverse the length of all separating cells, each like component as it exits will be rotationally displaced the same fixed angular distance from the point in space where the mixture was injected into the cells and it will therefore exit into the same collection compartment located at the fixed position.

The separated components of the mixture are individually collected in their respective collection compartments. An individual withdrawal tube or other means may be connected to each of the collection compartments which are fixed for removing a separated component from the collection unit, without the necessity of dismantling the unit or removing the membrane bags. The withdrawal of the collected components may be performed either continuously during the separating process or only after the mixture has completely been separated and collected.

SUMMARY AND OBJECTS

It is an object of this invention to provide apparatus for producing a continuous collection of separated components of a charged particle mixture using the preferred electrophoretic process and a supporting medium.

An additional object is to provide electrophoretic apparatus that continually separates a mixture into its individual components and collects the components in individual collection compartments, automatically without constant supervision by an operator.

An additional object is to provide such apparatus that is inexpensive and simple to operate.

Another object is to provide such apparatus that is reliable and has a minimum of electrical circuitry and mechanical parts.

A further object is to provide such a device that is portable and may be readily moved for use at different locations.

Other and further objects of the invention will be apparent from the following description taken in conjunction with the drawings appended hereto.

DESCRIPTION OF DRAWINGS

FIGS. 5($a$)–($e$) are a schematic depiction of a series of separating cells with the mixtures shown in different states of separation;

FIGS. 6($a$)–($d$) are a schematic depiction of a series of separating cells having more than one batch of mixture being separated simultaneously;

FIG. 7 is a perspective view of an alternative embodiment of the device of FIG. 1;

A PREFERRED EMBODIMENT

Figure 1:
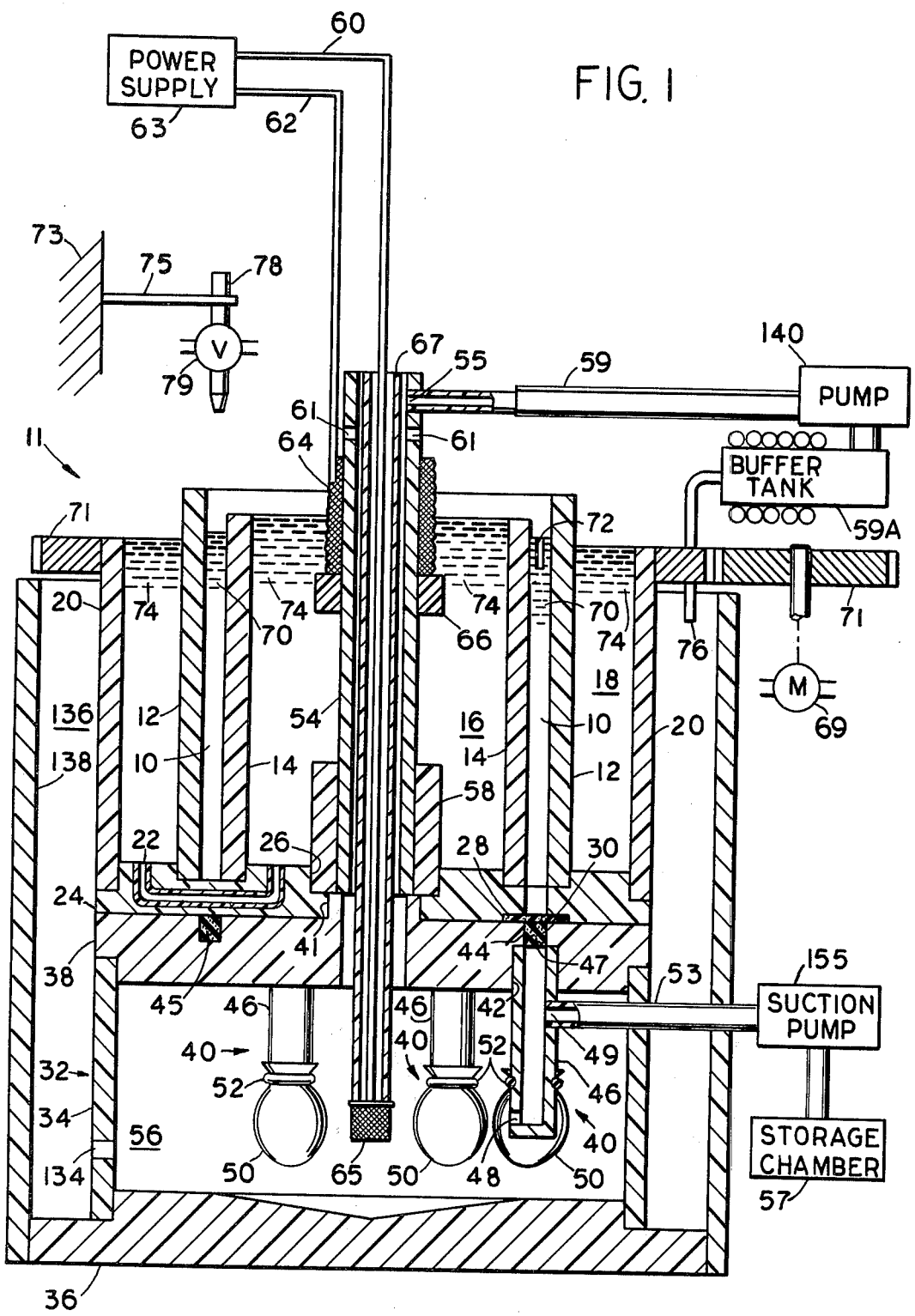
FIG. 1 is a cross-sectional elevational view of a preferred embodiment of the invention.
Figure 2:
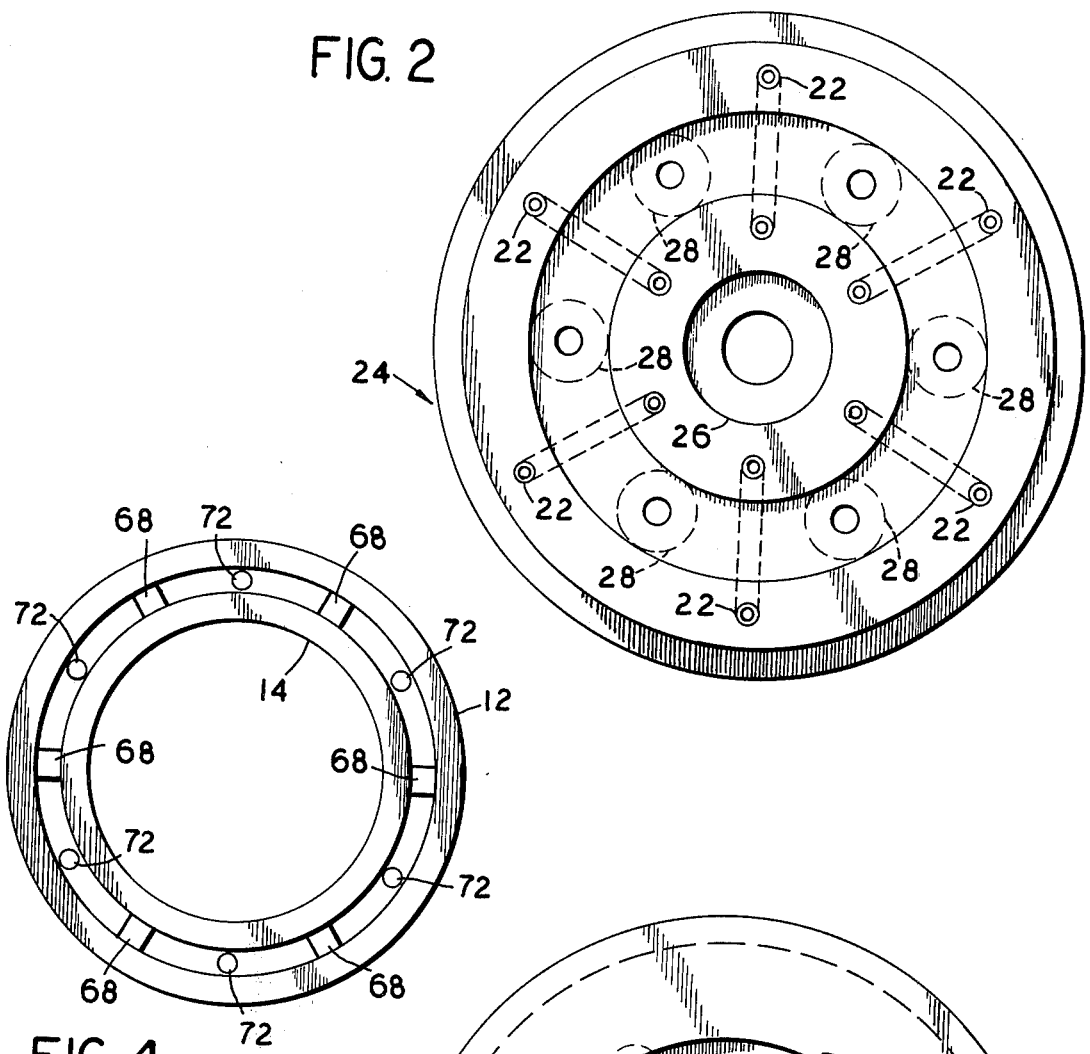
FIG. 2 is a top view of the supporting plate alone of the device of FIG. 1.

In FIG. 1, the separating unit 11, comprising an essentially annular separating chamber 10, is formed between two cylindrical walls 12 and 14 so as to form an interior buffer chamber 16. An exterior buffer chamber 18 is formed between a third cylindrical wall 20 and the outer portion of cylindrical wall 12 of the separation chamber 10. Buffer chambers 16 and 18 are suitably joined by a connecting passageway, such as a tube 22, passing through a supporting plate 24 upon which rest cylindrical walls 12, 14 and 20. The supporting plate 24, shown in FIG. 2, has a central countersunk aperture 26 and a series of countersunk apertures 28 equi-spaced peripherally from one another and directly below the separation chamber 10. The elements just described are made of any electrically insulating material, such as rubber or polyethylene or other plastic materials, non-reactive with respect to the separating medium and materials being separated.

Covering each aperture 28 in the supporting plate 24 is a thin porous retaining ring 30 of sponge or similar material which provides a bottom support surface for the supporting medium. This ring when saturated with electrolyte buffer solution has a very low electrical resistance, and will not restrict the passage of the separated components to the collection unit 32.

Located below the separating unit 11 is the collection unit 32 for collecting the separated components as they leave the separating unit 11. The collection unit 32 comprises a cylindrical wall 34, a base 36, a cover plate 38 and collection compartments 40, all of inert non-conducting material.

Figure 3:
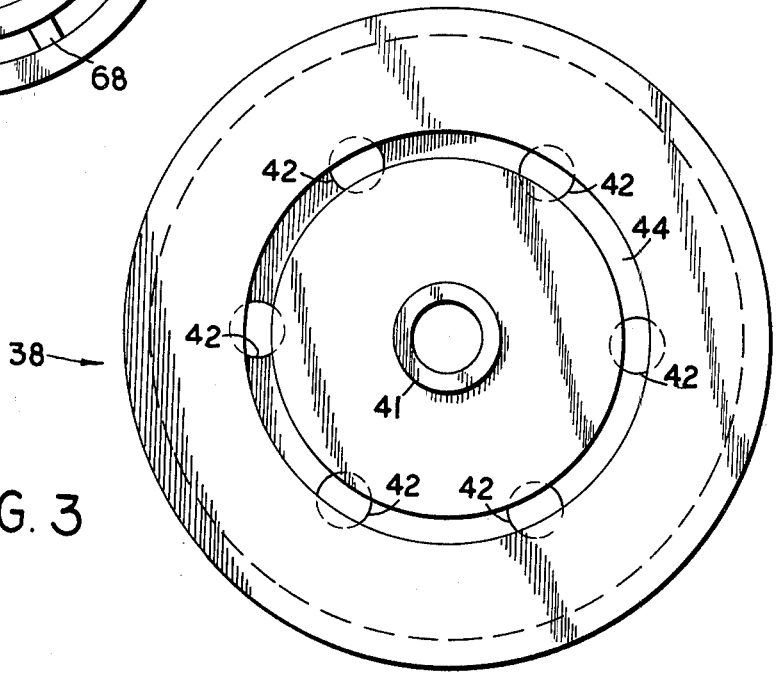
FIG. 3 is a top view of the cover plate of the collecting chamber alone of the device of FIG. 1.

The cylindrical wall 34 is covered by the cover plate 38, shown in FIG. 3, which has an inner projecting lip 41 of an outer diameter slightly less than the smaller diameter of the central aperture 26 of the supporting plate 24. The cover plate 38 also has a series of apertures 42 respectively corresponding to and communicating with the apertures 28 of the supporting plate. In addition, a circular groove 44, illustrated as having a square cross-section, is formed in the top surface of the cover plate 38 extending through the apertures 42 of the cover plate. Into this groove 44 in the cover plate 38 is placed a ring 45 of sponge or other conductive porous material, such as porous polyethylene, which serves to draw off the separated components into the collection compartments 40.

Each of the collection compartments 40 comprises an inert tube or cylinder 46, such as of a plastic material, having an open end 47 inserted into the bottom end of a corresponding aperture 42 in the cover plate 38. The tube 46 has one or more apertures 48 located in its side or end, which is otherwise closed. The apertures 48 are enclosed within a membrane bag 50 suitably sealed around tube 46 and having a pore size which permits the ions of the electrolytic buffer solution to pass freely, while restricting the passage of any proteins or other collected components. The membrane bag 50 may be sealably attached to the collecting member 46 by the use of an "O-ring" 52 or any other suitable sealing means, such as adhesives. It is preferable, however, that a readily removable sealing means be employed.

Each tube 46 also may have another aperture 49 into which is fitted a withdrawal tube 53 which is connected through a suction pump 155 to a final storage chamber 57 for the individual component being collected at that tube 46.

A hollow connecting member 54, made of an electrically non-conductive material, having a diameter smaller than that of the larger diameter of the central aperture of the supporting plate 24 and of a length at least as great as the height of the interior buffer chamber 16 is fitted in the aperture of the supporting plate 24 and rests on the projecting lip 41 of the collecting cover plate 38 so that access to the collection buffer chamber 56 may be had through the separating unit 11. A sleeve 58 rests on the lip of the supporting plate 24 slidably engaging connecting member 54 and provides a seal isolating the interior buffer chamber 16 of the separating unit 11 from the chamber 56 of the collecting unit 32. The hollow connecting member 54 has a side inlet 55 near its upper end above the height of the buffer chamber 16, which is connected by a tube 59 to a buffer reservoir 59A. One or more overflow apertures 61 are also present in the connecting member 54 above the height of the buffer chamber 16.

Electrodes 60 and 62, connected to the positive and negative terminals of a power supply 63 respectively, are present in the collection buffer chamber 56 and the interior buffer chamber 16. Each of the electrodes terminates in a screen 64 or 65 of a highly conductive material such as platinum or silver wire gauze. However, any well known conductive materials inert as to the materials to be separated and the buffer solution may be used. Electrode support ring 66 acts to support the electrode 64 in the interior buffer chamber 16. Electrode 60 is encased in an electrically non-conductive sheath 67.

The separating unit 11 with the exception of the connecting means 54, is connected by gears 71, friction drive or other means to a suitable motor means 69 for rotating the unit 11 about its longitudinal axis. The motor means 69 may continuously rotate the separating unit 11 or, as in a preferred embodiment, it may step the unit at fixed angular increments at fixed intervals of time.

A separating medium 70 of annular form is placed between the cylindrical walls 12 and 14. The walls 12 and 14 and retaining ring 30 form a chamber to retain the separating medium.

Cylindrical walls 12 and 14 are removable from the supporting plate 24 in order to facilitate the changing or installation of the separating medium. For example, when a gelatinous separating medium is to be used, the cylindrical walls 12 and 14 may be removed, an insert placed between these walls so as to create a bottom surface, and the medium in liquid form poured in. After the liquid solidifies, the entire chamber may be replaced in the separating unit. Notches or recesses 72 are formed in the solidified medium 70 at locations equi-distant along the top surface of the supporting medium, in registration with the apertures 28 and 42 of the supporting plate 24 and the cover plate 38. Such recesses 72 serve to avoid sideways dispersion of the input mixture when it is applied to the supporting medium 70. The notches or recesses 72 may be formed by any conventional method such as molding or the application of pressure. The recesses 72 are illustrated in FIG. 1 as having a rectangular cross section centrally located between the supporting walls 12 and 14 of the separating chamber. However, the recesses are not so limited. Any shape and location that serves to restrain the mixture from traveling in a lateral direction is sufficient. For example, a slot transverse to the support walls would operate equally as well as the illustrated embodiment.

Figure 4:
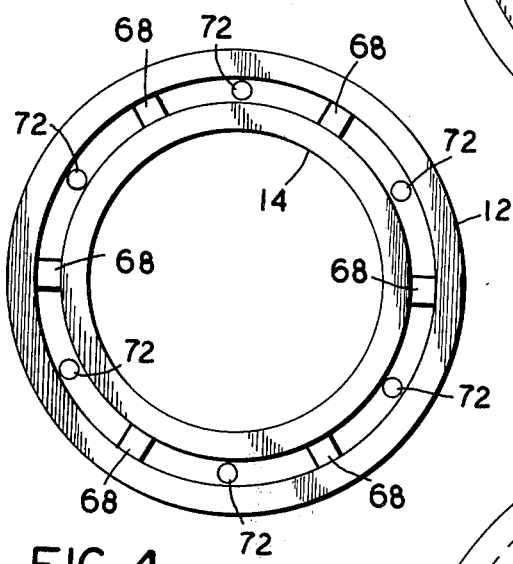
FIG. 4 is a top view of the separating chamber of FIG. 1 with partitions forming individual cells.

As an alternative, or in addition to creating recesses in the gelatinous supporting medium, it is possible to insert a series of inert vertical partitions 68, such as from a plastic material, between cylindrical walls 12 and 14 in order to break the separating chamber into individual cells, as shown in FIG. 4.

Using either the recesses 72 or the partitions 68, the mixture once introduced into the separating chamber will be constricted in its mobility to essentially the vertical direction. Any other means for limiting the dispersion of the mixture after placement in the separating medium, such as individual containers, may also be used.

The entire collection and separation units are inserted into a supplemental chamber 136 formed by the placing of a fourth cylindrical wall 138 on base 36. An opening 134 in the wall 34 of the collection unit joins the collection buffer chamber 56 with the supplemental chamber 136. One end of a siphon or pump tube 76 is introduced into the supplemental chamber 136 and the other end is connected to the large buffer tank 59A. The use of the supplemental chamber 136 ensures that the interface between the separation unit and the collection unit will not leak the buffer solution. However, leakproof seals, such as those made of rubber, may also be used to prevent any leaking.

When the separating medium is in a state ready to receive a mixture, an electrically neutral buffer solution 74 stored in the buffer tank 59A is pumped by pump 140 through the inlet 55 of the connection member 54 until the collection buffer chamber 56 is filled. The buffer solution overflows through apertures 61 of the connecting member and fills the interior, exterior and supplemental buffer chambers 16, 18 and 136 so that the top of the separating medium is in contact with and covered by the buffer solution.

The buffer solution is preferably maintained by a refrigeration system 77 at a temperature within the vicinity of 0°– 25°C, in order to prevent any gel supporting media from swelling or deterioration of mixture under the effects of heat which may be generated during the operation of the device. The buffer solution is slowly circulated in any suitable manner throughout the system including the collection unit 72, the buffer tanks 59A and the buffer chambers 16 and 18 of the separating unit.

The buffer solution in the chambers 16 and 18 of the separating unit 11 is electrically insulated from the buffer solution in the collection buffer chamber 56. The buffer solution in the separating unit 11 is usually maintained at a more negative potential while the buffer solution in the collecting unit is maintained at a more positive potential, so that a potential difference creating an electric field is maintained across the supporting medium as required in the process of electrophoresis. Of course, the polarity of the electrical source may be reversed so that the separating unit chambers are maintained at a positive potential while the collecting unit chamber is maintained at the negative potential, depending on the pH of the buffer solution and the materials being separated. The pH of the buffer is maintained constant because of the large capacity of the buffer reservoir and by neutralization of acids and bases produced at the electrodes by mixing during buffer circulation.

The application 78 may be any of the conventional devices, such as a plunger or any other well known fluid injection or control device, such as are used to control the flow of fluids. The applicator 78 is positioned above the separating chamber 10 in fixed relation to the collecting unit 32, and in conventional manner is capable of providing discrete batches of the mixture by the operation of fluid control valve 79. The applicator 78 is illustrated in FIG. 1 as being held by rod 75 which is attached to fixed support 73. However, the applicator 78 may be fixed directly to the collection unit 32 or to base 36.

In the operation of the apparatus, the applicator 78 is activated so that a batch of the input mixture is deposited in one of the cells. The mixture to be separated preferably has a non-polar material, such as sucrose, added to it to minimize dispersion in the buffer solution by increasing its density.

At fixed intervals of time the separating unit is rotatably stepped about its longitudinal axis when a second cell comes into registration with the applicator, again a batch of the mixture is deposited onto the supporting medium of that cell, the apparatus continues in this manner of operation, continually applying the mixture onto the successive cells or recesses of the separating medium at fixed intervals of time.

The mixture is composed of components which may become positively or negatively charged, depending on the pH of their environment. As is well known, such particles have varying constants of mobility in a supporting medium when placed in the influence of an electric field. Accordingly, the components will migrate in a vertical direction from the top of the supporting medium to the bottom at respectively different constant speeds depending on the charge, molecular size and weight of each component. However, each like component travels at the same speed. Therefore, after a fixed period of time each like-charged component will have traveled the same vertical distance, thus creating a distinct spatial separation in the separating medium between different components.

FIGS. 5(a)–(e) show schematically the apparatus of FIG. 1 with separating cells 80–85 and collection compartments 86–91 arranged in a linear configuration, under the influence of an electrical field. In FIG. 5(a), the mixture to be separated is shown as just being applied to cell 80 at a time $t_o$. In FIG. 5(b), the mixture is shown as being applied to chamber 81 at time $t_1$ after the cell 81 has been shifted so as to come into registration with the applicator 78. The applicator 78 and the collection compartments 86–95 remain fixed. In cell 80 is shown the resulting separation between components 96 and 98 after a time $t_1$. The component 96 has been assumed to travel only one half the distance of component 98 in the same interval of time.

FIG. 5(c) shows the situation at time $t_2$. The component 96 in cell 80 has traveled a total of 2 distance units while component 98 has traveled 4 distance units and is in the process of exiting the cell into collection compartment 88. Mixture continues to be applied to the next separating cell 82 as it is brought into registration with the applicator 78.

In FIG. 5(d), at time $t_3$, component 98 of cell 81, which was applied at time $t_1$, has traversed the length of the cell and also is in the process of being deposited into collection compartment 88.

Meanwhile, at time $t_4$, shown in FIG. 5(e), the component 96, which was applied to cell 80 at time $t_o$, is exiting cell 80 into collection compartment 86. In the same way, each of the succeeding separating cells will deposit all of its components 98 into collection compartment 88, and all of its component 96 into collection compartment 86.

It should be noted that in the above example, illustrated in FIGS. 5(a)–(e), only two components 96 and 98 were indicated as being present in the mixture. Therefore, there are only two exit points from the separating cells and only two collection compartments 86 and 88 were required. It should be recognized, however, that any number of components may be present in the mixture to be separated and that collection compartments corresponding to individual exit points for each of the components may be provided.

It is not required that on loading, the supporting medium be completely devoid of any of the mixture introduced into it during a previous application. In FIGS. 6(a)–(d) is shown a series of instantaneous views of separating cells arranged in a linear configuration, at varying times from $t_5$ to $t_8$ to show more readily how more than one application of the mixture may be in the process of separation and collection in the same separation cell at the same time. In these figures, it is assumed that the separating cells 101 to 106 are stationary while the applicator 78 and collection chambers 86, 88 are movable.

In FIG. 6(a), at time $t_5$, the mixture has just been applied to separating cell 106. Cells 101 to 105 were assumed to have been loaded at earlier times $t_o$ to $t_4$, respectively, and show how the faster components 98 and slower component 96 have progressed and are being separated. Component 98 is in the process of exiting into collection chamber 88. In FIG. 6(b), the next batch of mixture to be separated has been introduced into separating cell 101 while component 96 has not yet completely traversed the separation cell 101. As may be seen in FIGS. 6(c) and (d), component 96 continues to progress until it exits into collection compartments 86 at $t_8$.

It is also possible for a component particle having a greater constant of mobility to catch up and mix with a component having a slower constant of mobility which was introduced into the separating cell at an earlier time. Provided that there is enough of a length of separating cell remaining before the depositing of the components into the collection compartments the faster component will merely pass through the slower one and still be deposited in its own collection compartment with no deleterious effects on its separation. However, where the point of remixing is essentially at the point of collection no separation of the two particular components involved will occur. All other components in the mixture, however, will be separated.

While in the preferred embodiment of the invention, the mixture to be separated is introduced into the separating chamber in discrete batches, it is possible for a continuous flow of the mixture to be introduced onto the supporting medium. While it may appear that such an introduction will result in a non-uniform separation of the components, thereby effecting their purity, this is not true. Upon settling upon the supporting medium the mixture immediately assumes a uniform distribution over the entire available surface of the medium, which is the top of one cell. Therefore, further introduction into the separating chamber of the mixture to be separated will still yield a substantially uniform separation of charged particles. In any event, as long as the mobility of the different components is sufficiently distinct, the relative displacement of the different components will still be large enough to avoid any mixing between them at a collection point.

ALTERNATIVE EMBODIMENTS

In the above description of the preferred embodiment of the invention, it was the separating unit 11 that was rotated while the applicator 78 and the collection unit 32 remained stationary. It should be recognized that in these forms of the invention only relative motion between the collection unit and the separating unit is necessary for the operation of the invention. Hence, many variations of the preferred embodiment may be utilized without departing from the scope or spirit of the invention. For example, the separating unit 11 may be held stationary while the applicator 78 and the collection unit 32 are shifted sequentially, without any change in the mode of operation of the device.

It is also possible to use a series of applicators 78, as shown in FIG. 7, instead of only one. In this embodiment of the invention, the applicators would be sequentially activated by a control circuit 112 to sequentially deposit the mixture in each of the cells of the separating unit.

It is not essential that the separating and collector units be arranged in a closed loop configuration. For example, the separating cells may be arranged in a linear configuration with either a single applicator mounted on a rod or a series of applicators, individually controlled, depositing the mixture into the separating cells. The collection compartments, arranged in either a linear or a closed loop configuration below the separating cells, sequentially collect the separated components as the components exit the separating cells.

It will be understood that the only important relationship among the cells, applicator means and collector means is that the applicator means should load the cells sequentially, and the collector means should collect from the cells in the same sequence, with a fixed time interval between loading each cell and collecting from that same cell.

Figure 8:
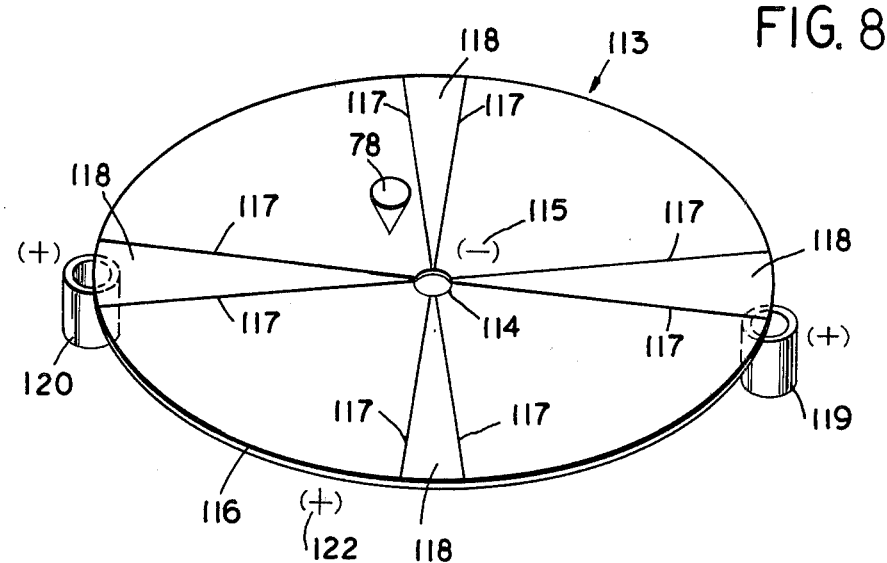
FIG. 8 is a perspective view of an alternative embodiment of the invention.

It should be clear that other than the vertical cylindrical chamber of supporting media may be used without departing from the basic concept and scope of the invention. In particular a disclike configuration 113 shown in FIG. 8 may be used with the center of the disc 114 maintained at one potential 115 and the periphery of the disc 116 maintained at the opposite potential 122. Partitions 117 extend radially from the center of the disc creating individual compartments 118. The collection compartments 119, 120 are located at the periphery of the disc.

During operation the disc rotates with the mixture being deposited sequentially by an applicator 78 into the compartments at a point near the center of the disc. The component particles as they migrate toward the periphery of the disc define essentially a spiral, in space, as opposed to the helix of the cylindrical configuration. The components reach the periphery of the disc at a fixed radial displacement and are collected by individual collection compartments 119 and 120.

As in the cylindrical configuration any supporting media, such as paper, may be used. When a paper disc is used instead of a gel, such as in high voltage electrophoresis, there is no need for partitions to restrain the migration of the component particles. A deposit of the mixture to be separated applied to the paper will still travel the path of a spiral and have its components deposited in fixed collection compartments.

Figure 9:
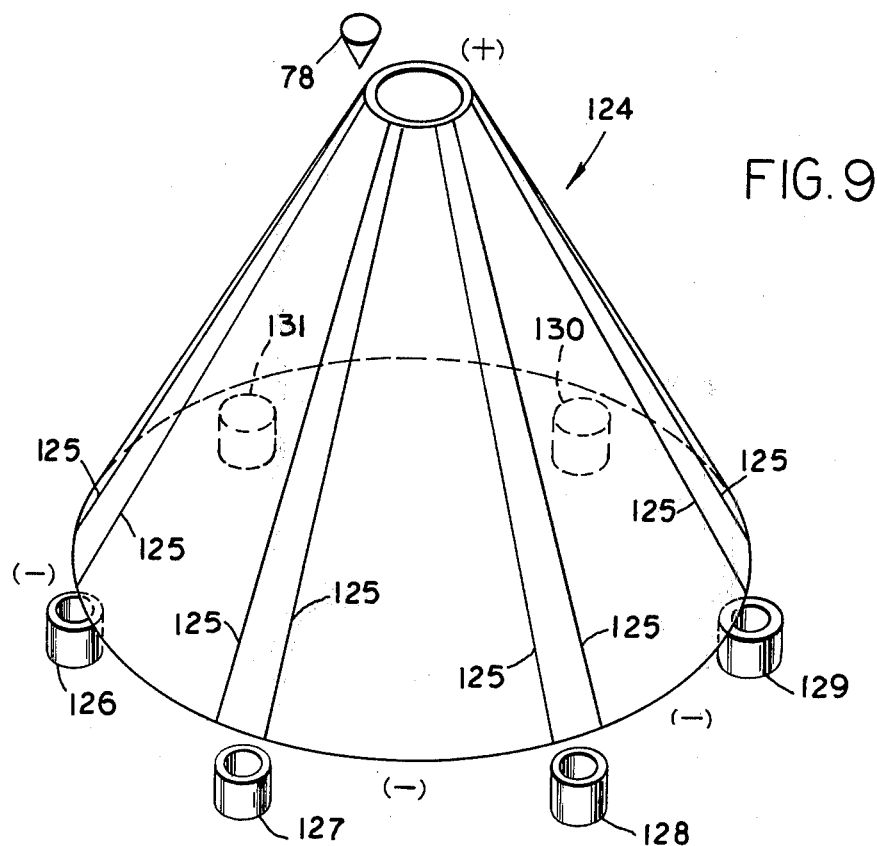
FIG. 9 is a perspective view of an alternative embodiment of the invention.

Also, any geometric configuration between the extremes of a cylinder and a disc may be used. For example, a conic structure 124 shown in FIG. 9, may be employed without any change in the manner and theory of operation of this invention. Again, partitions 125 may serve to maintain separation of the mixture during operation. The compartments 126–131 collect the separated components in the same manner as in the other embodiments.

What is claimed is:
1. Apparatus for continuously electrophoretically separating and collecting the individual components of a mixture where such components have differing electrophoretic mobility rates comprising:
   a separation chamber comprising
   an electrophoretic supporting medium having a plurality of separating cells, each cell having an input and an output;
   an applicator arrangement for supplying to each cell input in predetermined sequence an amount of said mixture;
   a collector arrangement cooperating with said cell outputs in said same sequence for collecting discharge successively from said outputs; and
   a power supply for inducing an electrical potential difference between said inputs and said outputs of said cells.
2. The apparatus of claim 1, wherein the cells comprise two walls defining an annular space between said walls for containing the supporting medium.
3. The apparatus of claim 2 in which a series of vertical partitions are located between said walls thereby forming the several separating cells.
4. The apparatus of claim 2 in which a plurality of recesses are located on the inputs surface of the supporting medium thereby forming the several separating cells.

5. The apparatus of claim 1 comprising a plurality of applicators operable sequentially to deposit the mixture into each of the separating cells in sequence.

6. The apparatus of claim 1 in which the applicator arrangement has means for depositing amounts of the mixture to be separated into the separating cells at fixed intervals of time.

7. The apparatus of claim 1 in which each collector comprises a tube having a component-receiving aperture for receiving the separated component from the separating cell output and a second aperture, said second aperture being sealably enclosed by a membrane of a material capable of retaining the collected components but passing ions of an electrolytic solution.

8. The apparatus of claim 7 in which each of said collectors includes means for withdrawing the collected component from the membrane enclosure.

9. The apparatus of claim 1, wherein the cells of electrophoretic supporting medium comprises two walls defining a right circular cylinder between said walls for containing the supporting medium.

10. The apparatus of claim 1, wherein the cells of electrophoretic supporting medium comprises two walls defining a truncated conic annular space between said walls for containing the supporting medium.

11. Apparatus for continuously electrophoretically separating and collecting the individual components of a mixture where such components have differing electrophoretic mobility rates comprising
a circular disc of a separating medium, said disc having a center and a periphery, said disc having a plurality of compartments each extending between said center and said periphery, each of said compartments having an input and an output;
a power supply for inducing an electrical potential difference between said inputs and said outputs;
an applicator for supplying the mixture to be separated to the inputs in a predetermined sequence;
a collector cooperating with said disc in said same sequence for collecting the separated components as said components discharge at an output.

12. Apparatus for continuously electrophoretically separating and collecting the individual components of a mixture where such components have differing electrophoretic mobility rates comprising:
a plurality of separating cells of an electrophoretic supporting medium, each of said cells having an input and an output;
an applicator arrangement for supplying to each of said cell inputs given amounts of said mixture in a predetermined sequence;
a collector arrangement cooperating with said cell outputs, with substantially equal time intervals between the deposit of said mixture into each of said cells and the collection from the same cell; and
a power supply for inducing an electric potential difference between said input and said output of each of said cells.

13. Apparatus as recited in claim 12 further comprising:
means for moving said separating cells.

14. The apparatus as recited in claim 12 further comprising:
means for moving said applicator arrangement; and
means for moving said collector arrangement.

* * * * *